United States Patent [19]

Buuck et al.

[11] Patent Number: 5,513,659
[45] Date of Patent: May 7, 1996

[54] INCONTINENCE DEVICE

[75] Inventors: Robert E. Buuck, Minnetonka; Dezso K. Levius, Bloomington, both of Minn.

[73] Assignee: Iotek, Inc., Minneapolis, Minn.

[21] Appl. No.: 407,267

[22] Filed: Mar. 20, 1995

Related U.S. Application Data

[63] Continuation-in-part of Ser. No. 328,331, Oct. 24, 1994, abandoned.

[51] Int. Cl.⁶ ...................................................... A61F 5/48
[52] U.S. Cl. ............................ 128/885; 128/DIG. 25; 600/29
[58] Field of Search .......................... 128/885, DIG. 25; 600/29–31

[56] References Cited

U.S. PATENT DOCUMENTS

| | | | |
|---|---|---|---|
| 2,649,854 | 8/1953 | Salm | 600/29 |
| 3,372,695 | 3/1968 | Beliveau | 128/DIG. 25 |
| 3,646,929 | 3/1972 | Bonnar . | |
| 3,777,748 | 12/1973 | Abramson | 128/840 |
| 3,783,861 | 1/1974 | Abramson | 128/840 |
| 3,812,841 | 5/1974 | Isaacson | 600/29 |
| 3,841,304 | 10/1974 | Jones . | |
| 4,652,259 | 3/1987 | O'Neil . | |
| 4,850,963 | 7/1989 | Sparks | 128/DIG. 25 |
| 4,867,149 | 9/1989 | Falco . | |
| 5,030,199 | 7/1991 | Barwick et al. . | |
| 5,082,006 | 1/1992 | Jonasson | 600/29 |
| 5,090,424 | 2/1992 | Simon et al. . | |
| 5,131,906 | 7/1992 | Chen . | |
| 5,147,301 | 9/1992 | Ruvio | 600/29 |
| 5,380,268 | 1/1995 | Wheeler | 128/DIG. 25 |

OTHER PUBLICATIONS

Article entitled "The Linear Everting Catheter: a Nonhysteroscopic, Transvaginal Technique for Access in Microendoscopy of the Fallopian Tube", vol. 58, No. 4, Oct., 1992.

*Primary Examiner*—Michael A. Brown
*Attorney, Agent, or Firm*—Merchant, Gould, Smith, Edell, Welter & Schmidt

[57] ABSTRACT

An incontinence plug includes an anchor for positioning within a patient's bladder and a flow blocking enlargement for acting in sealing engagement against a urethral wall. A protective sleeve prevents contact between the distal end of the plug and an entrance end of the urethra to prevent transportation of pathogens from the entrance of the urethra toward the bladder.

10 Claims, 6 Drawing Sheets

INCONTINENCE DEVICE

This is a continuation-in-part, of application Ser. No. 08/328,331, filed Oct. 24, 1994 now abandoned.

BACKGROUND OF THE INVENTION

1. Field of the Invention

This invention pertains to an incontinence device. More particularly, this invention pertains to a female incontinence device for insertion into the urethra.

2. Description of the Prior Art

Female incontinence is a very common problem. Women suffering from incontinence experience a disruption in both their professional and recreational activities. Further, incontinence is detrimental to the self esteem of the patient.

Incontinence control devices for insertion into the urethra are known in the prior art. Examples of such include those shown in U.S. Pat. Nos. 5,090,424 and 5,082,006. For a female incontinence device to be effective and to be used by a large number of patients, the design should accomplish several objectives. The device should restore continence to an acceptable level in the majority of patients for whom it may be prescribed. The incontinence device must be used with a minimum of complications. The more serious complications include U.T.I. and hematuria. The incontinence device should be insertable into the urethra by the patient with a minimum of physical and social discomfort. Also, the incontinence device must be designed in such a manner and with materials acceptable to the Food and Drug Administration, so that the device can be produced, packaged and sterilized at low cost.

II. SUMMARY OF THE INVENTION

According to a preferred embodiment of the present invention, an incontinence device includes a plug sized to be inserted at least partially into a urethra. The incontinence device includes a protective sleeve surrounding the plug and having at least a first portion sized to extend into the urethra as the plug is inserted into the urethra with the plug extending beyond the first portion when the plug is fully inserted into the urethra. Additional embodiments of the present invention include an incontinence plug which has a flexible body with a distal end and a proximal end. The length between the distal end and the proximal end is selected for the distal end to extend beyond a bladder opening when the proximal end is positioned against the patient's meatus. The plug includes an anchor carried adjacent the distal end.

IV. DESCRIPTION OF THE PREFERRED EMBODIMENT

With reference now to the various drawing figures in which identical elements are numbered identically throughout, a description of the preferred embodiment will now be provided.

Figure 1:
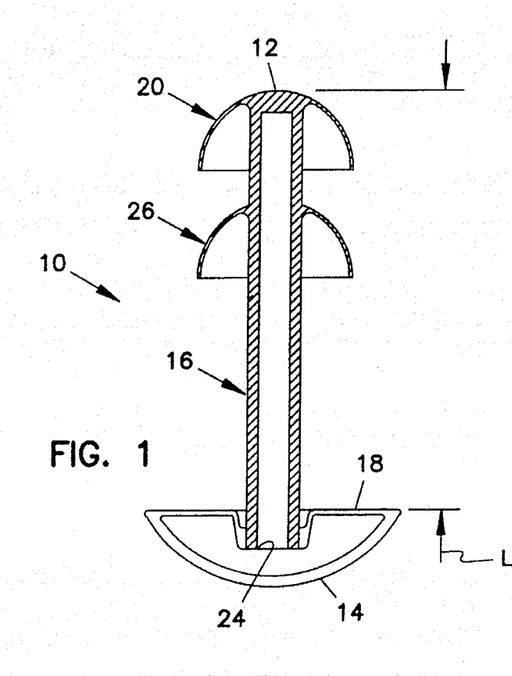
FIG. 1 shows an incontinence plug shown in cross section.

With initial reference to FIG. 1, an incontinence plug 10 is shown having a distal end 12 and a proximal end 14. The distal end 12 and proximal end 14 are connected by a shaft 16. The distal end 14 is provided with a flange 18.

The shaft 16 is sized to be inserted into a urethra with the flange 18 abutting a patient's meatus. The length of the shaft 16 is selected such that the distal end 12 projects beyond a bladder neck when the flange 18 is placed against the meatus. Typically, an adult female urethra has a length of three to five centimeters. Accordingly, to accommodate a wide range of female patients, three to four sizes of shaft 16 will be provided in a preferred embodiment such that a prescribing physician can select the appropriate size to ensure that with a particular patient, the distal end 12 projects into the bladder neck when the flange 18 is placed against the meatus.

The distal end 12 is provided with an anchor 20 in the form of a semi-spherical cap which, in a rest state shown in FIG. 1, projects rearwardly toward the flanged proximal end 14. The shaft 16 is hollow to present a central core 22. Further, an opening 24 is formed through the distal end 14 with the opening 24 aligned with the core 22.

In a preferred embodiment, the entire plug 10 is integrally formed of silicone rubber material. With an injection molded plug 10, the anchor 20 projects rearwardly as shown in FIG. 1. However, the positioning of the anchor 20 can be reversed (for example, to the position and shape of anchor 20" in FIG. 3) where the anchor 20 is still semi-spherical in shape but projecting away from the flange 18. Further, a flow blocking member 26 is disposed between the anchor 20 and the flange 18. In the embodiment of FIG. 1, the flow blocking member 26 is shown of like construction as the anchor 20.

In a preferred embodiment, the length L of the plug is 30 millimeters. The diameter of the shaft is 6 millimeters and the diameter of both the anchor 20 and the flow blocking member 26 are silicone rubber. With the structure thus described, the distal end 12 is inserted into the urethra by a patient and the plug 10 is fully inserted at which point the flange end 18 is abutting the patient's meatus. With a properly sized plug 10, at full insertion of the plug 10, the anchor 20 passes through the bladder neck resulting in the anchor 20 assuming the reverse shape (e.g., that shown by anchor 20" in FIG. 3). Accordingly, the anchor 20 is received within the bladder to resist movement of the plug 10 out of the urethra. Further, when fully inserted the flow blocking member 26 is pressing against the wall of the urethra to block fluid flow through the urethra.

Figure 1A:
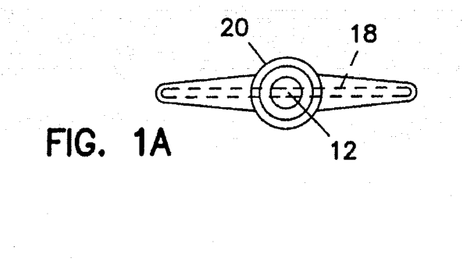
FIG. 1A is an end view of the plug of FIG. 1.
Figure 1B:
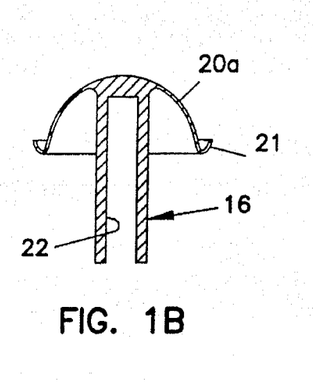
FIG. 1B is a cross-sectional view of an alternative embodiment to a distal end of the plug of FIG. 1.

An alternative to the embodiment of FIG. 1 is to eliminate the flow blocking member 26 and have anchor 20 provide both anchoring in the bladder and sealing at the bladder neck. FIG. 1B shows an alternative design of anchor 20. In FIG. 1B, alternative anchor 20a is provided with an upturned peripheral edge 21 to enhance sealing within the bladder.

Figure 2:
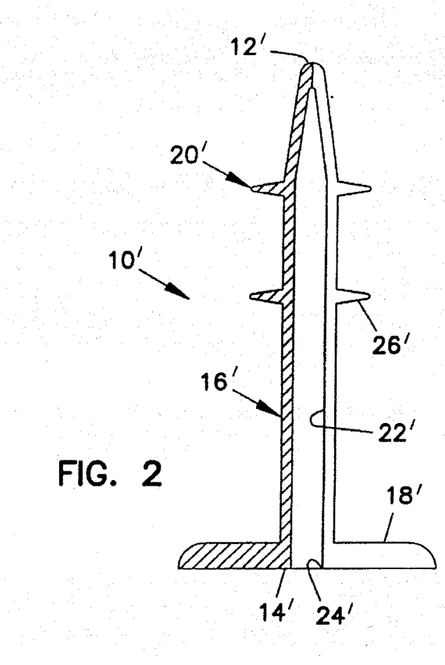
FIG. 2 is a view similar to FIG. 1 showing an alternative embodiment of the present invention.
Figure 2A:
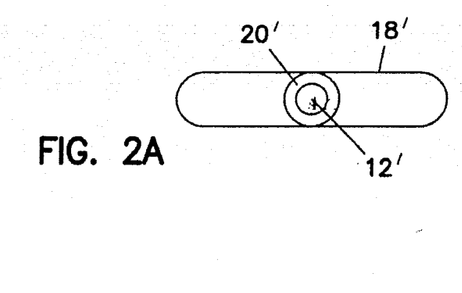
FIG. 2A is an end view of the embodiment of FIG. 2.

FIGS. 2 and 2A show an alternative embodiment of the present invention. Elements corresponding to those of FIGS. 1 and 1A are numbered identically with the addition of an apostrophe in the embodiment of FIGS. 2 and 2A to distinguish from the features of FIGS. 1 and 1A. In FIG. 2, the proximal end 14' is provided with a flange 18'. Near the distal end 12' is an anchor 20'. The anchor 20' is spaced from the flange 18' to project beyond the bladder neck and anchor the distal end 12' within the bladder. Further, a flow blocking member 26' is provided between the anchor 20' and the flange 18'. In the embodiment of FIGS. 2 and 2A, both the anchor 20' and flow blocking member 26' are integrally molded radially extending flanges.

Figure 3:
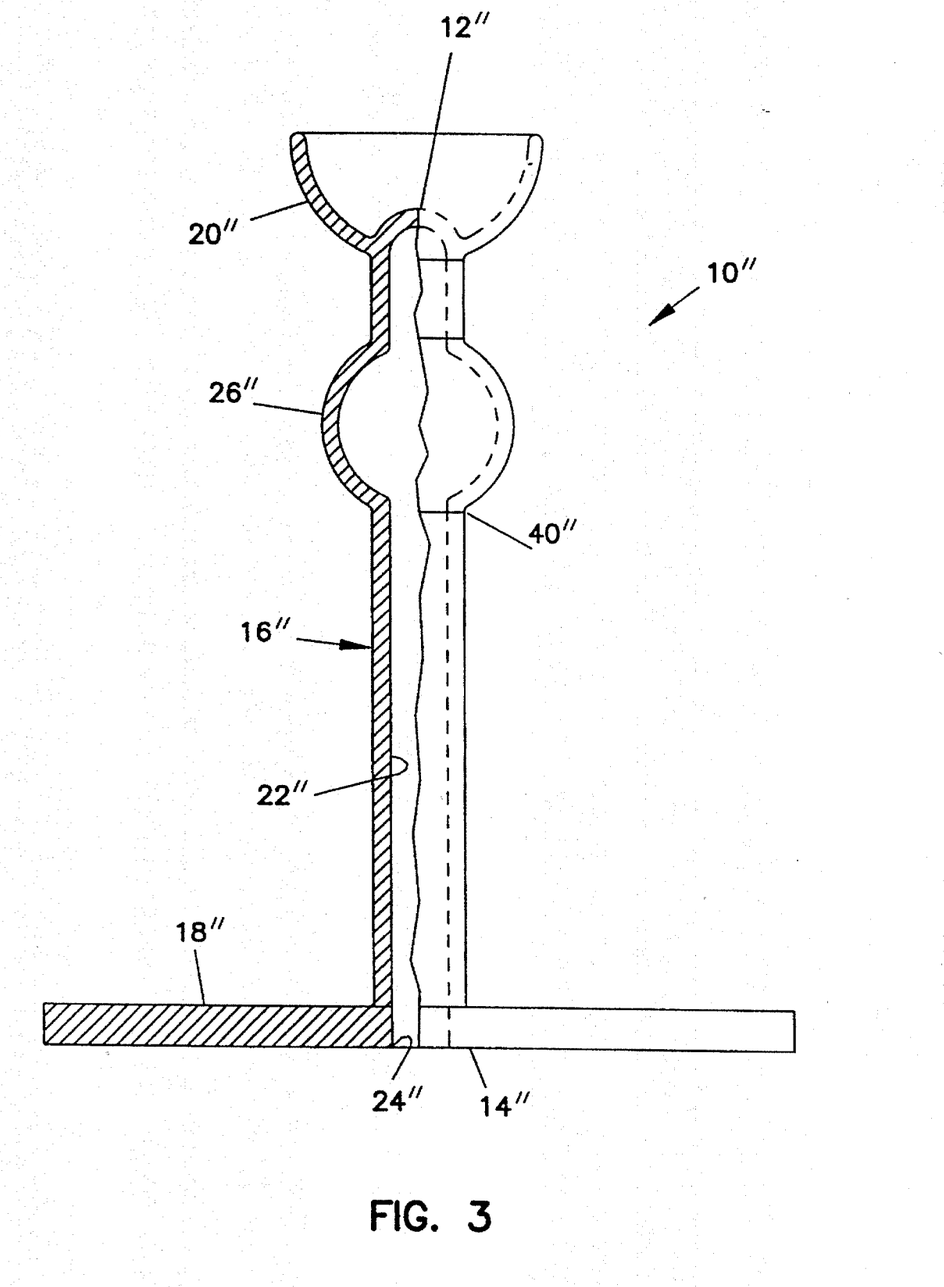
FIG. 3 is a view similar to FIG. 1 showing a still further alternative embodiment of the present invention.

FIG. 3 shows still a further and preferred embodiment of the present invention. In FIG. 3, elements corresponding to those of FIG. 1 are shown identically numbered with the addition of a double apostrophe to distinguish from FIG. 1.

In FIG. 3, the plug 10" extends from a proximal end 14" to a distal end 12". This length is approximately 39 mm. The anchor 20" is attached near the distal end 12". The distance from the point of attachment to the flange 18" is 338 mm to ensure that the point of attachment is just beyond the bladder neck of the patient when the plug 10" is fully inserted into the urethra with the flange 18" abutting the meatus of the patient. The outside diameter of the shaft 16" is 26 mm to ensure easy insertion into the urethra. In the embodiment of FIG. 3, the flow blocking member 26" is a spherical expansion of the shaft 16" and preferably having an outside diameter of 800 mm. As shown in FIG. 3, the anchor member 20" is semi-spherical projecting away from the flange 18" (but, like anchor 20 in FIG. 1 may be reversed). The entire device is injection molded silicone rubber. As a result, the device is flexible and non-traumatic upon insertion.

The bulb-shaped flow blocking member 26" is soft and pliable. It has a bottom end 40" which preferably is placed about 205 mm above the flange 18" to ensure placement of the flow blocking member 26" above the sphincter muscle in the urethra.

Figure 4:
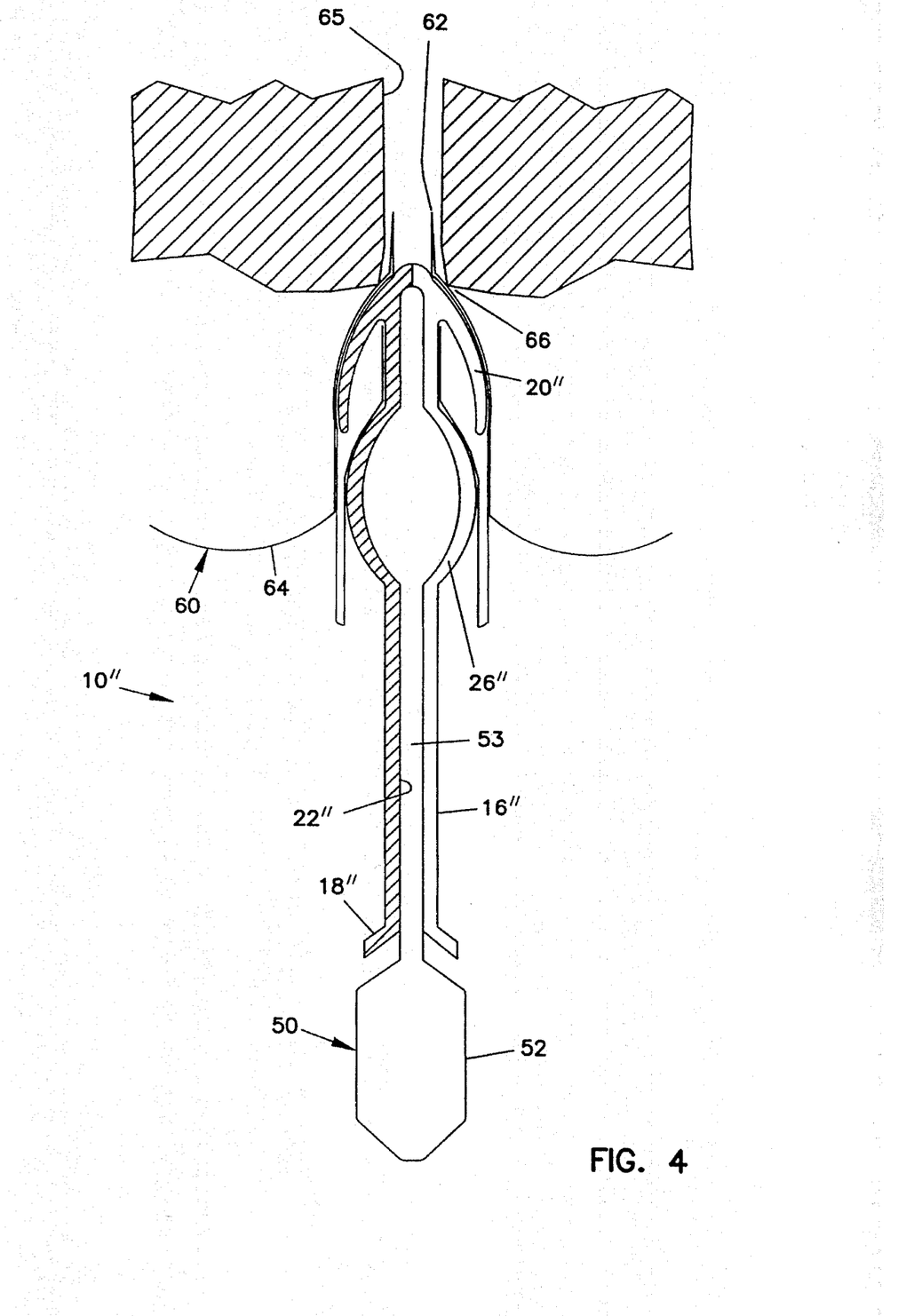
FIG. 4 is a view of a plug in combination with a protective sleeve just prior to insertion into a urethra.

To insert the device into the urethra, a generally rigid insertion pin 50 is provided as shown in FIG. 4. Pin 50 has a handle 52 to be grasped by a user and an extending pin 53 sized to be slidably received within the core 22" of shaft 16" of the embodiment of FIG. 3.

Figure 5:
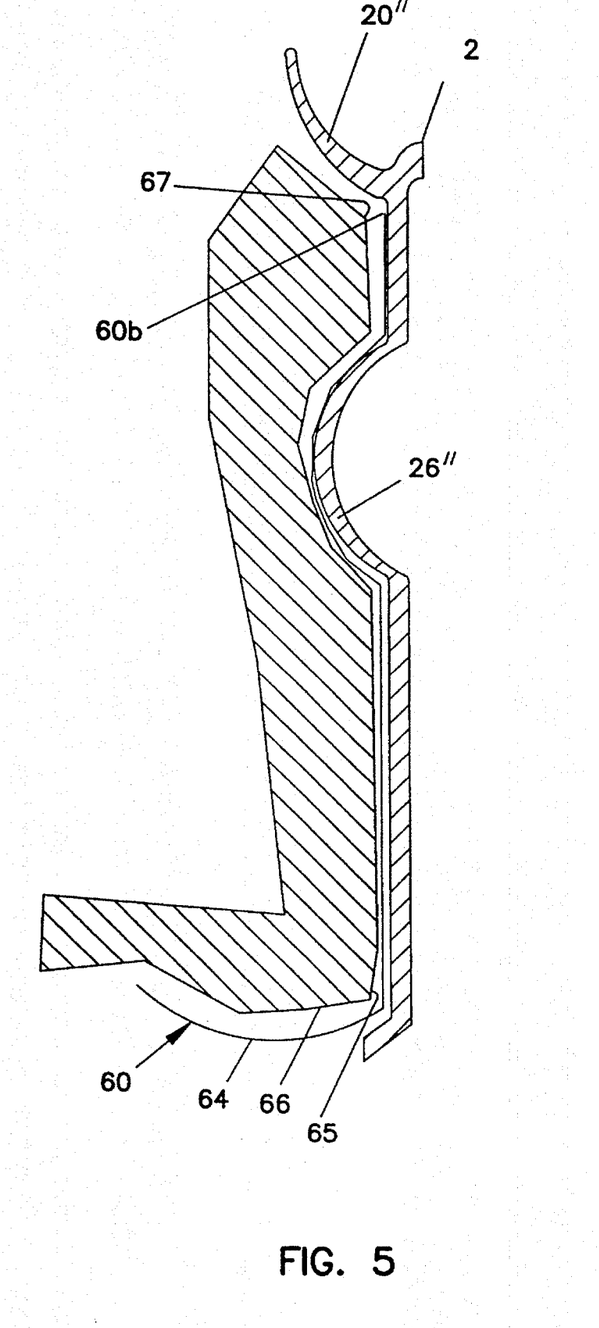
FIG. 5 is a view showing full insertion of the plug and sleeve into a urethra showing only a left half of an assembly so inserted with the right half being identical.

FIG. 4 shows insertion of the device into the urethra. In FIG. 4, the device is shown placed within a protective sleeve 60 which will be discussed in greater detail. The sleeve 60 has a distal end 62 which is open and a proximal end 64 which is open. The sleeve 60 is generally funnel-shaped. Placement of the distal end 12" of the device into the sleeve 60 causes the anchor 20" to bend backwards such that it is projecting toward the flange 18" as shown in FIG. 4. The device is then inserted into the urethra 65. Both the sleeve 60 and the plug 10" simultaneously advance into the urethra 65 until such time as the flange 64 comes in contact with the meatus 66. At this point, further advancement of the sleeve is blocked and the plug 10", upon further insertion, is forced out of end 62. Upon complete insertion into the urethra, as shown in FIG. 5, the anchor 22" extends beyond the bladder neck 67 and the resiliently formed anchor 22" assumes its rest shape as shown in FIG. 5. Further, at this insertion, the flow blocking member 26' is inserted above the positioning of the sphincter. When the plug is fully inserted, the pin 50 may be removed and discarded. The plug 10" provides incontinence control by means of the flow blocking member 26" pressing against the urethral wall and blocking fluid flow through the urethra. The plug 10" is retained within the urethra by means of the anchor 20" acting against the bladder neck 67. Also, the sleeve 60 is fully extended to separate the plug 10" from contact with the wall of the urethra 65.

It will be noted that the present invention, in a preferred embodiment, utilizes sleeve 60 to prevent contact between the distal end of the plug and the urethral wall until after the distal end has been moved at least halfway into the urethra. The use of the sleeve 60 prevents urethral or bladder infection. Specifically, without a sleeve 60, as a plug is inserted into the urethra, the plug can be in contact with bacteria or other pathogens which reside in the region of the meatus. Further insertion of the plug into the urethra can result in transporting those pathogens along the length of the urethra and into the bladder. The length of the sleeve is selected such that upon full insertion it extends at least half the length of the urethra. Preferably, the sleeve is formed of silicone, Teflon or the like which is sterile and lubricious or provided with a lubricious coating.

Figure 4A:
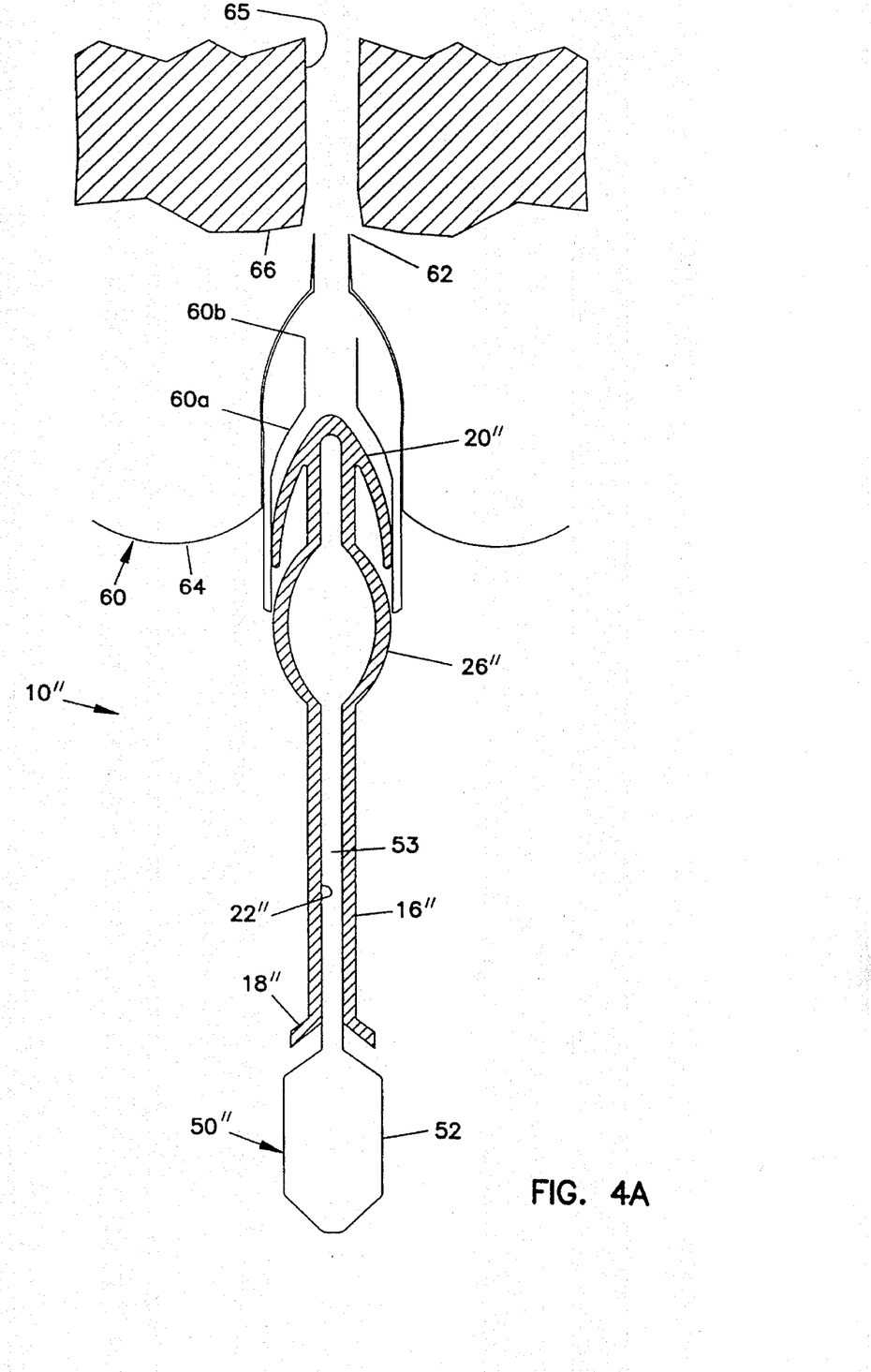
FIG. 4A is an alternative presentation of FIG. 4 with various elements shown in exaggerated size to further illustrate the present invention.

FIG. 4A best illustrates the sleeve 60 with part sizes exaggerated to illustrate the concept of the invention. Sleeve 60 is a rolling sleeve which includes a portion 60a folded into the sleeve 60. Portion 60a is attached to shaft 16" at the point of attachment 60b of the anchor 20". Therefore, as the sleeve 60 and plug 10" are inserted into the urethra the distal end 62 of the sleeve extends into the urethra 65 about half the length of the urethra. At this point, sleeve flange 64 abuts the meatus such that distal end 62 may not advance further. Continued insertion of the plug 10" forces sleeve portion 60a to be forced into the urethra beyond end 62. As a result, pathogens at the meatus which come in contact with end 62 can only be advanced halfway into the urethra and no further. The remaining portion 60a of the sleeve which contacts the urethra near the bladder is never in contact with the meatus.

Figure 6:
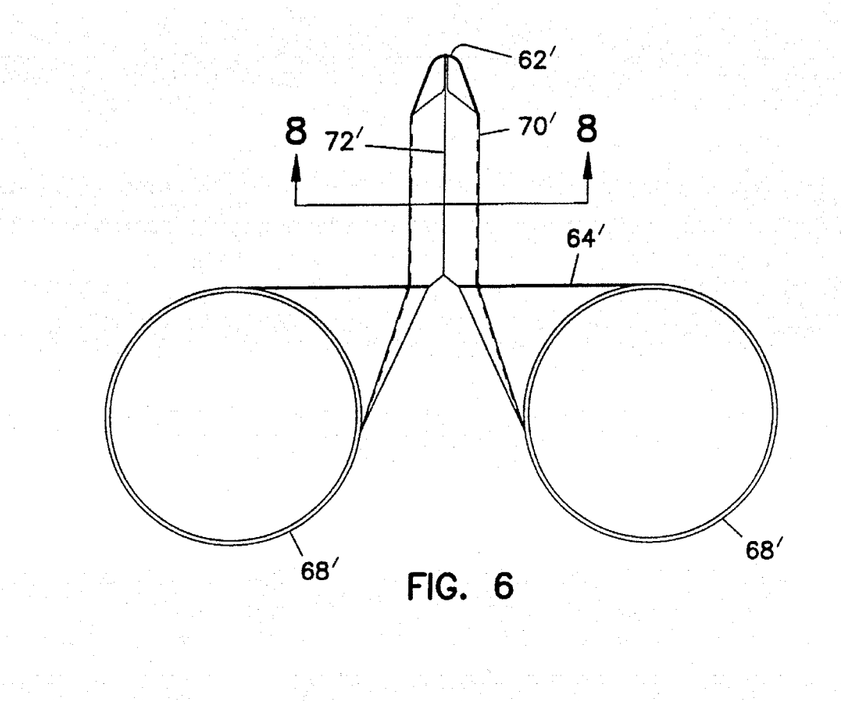
FIG. 6 is a side elevation view of an alternative embodiment of a protective sleeve for the present invention.
Figure 7:
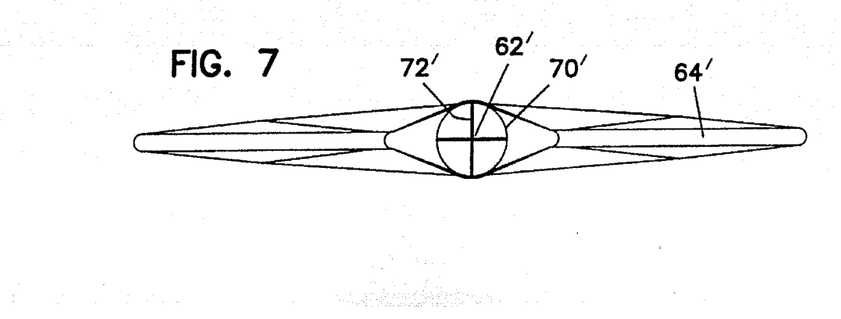
FIG. 7 is an end view of the sleeve of FIG. 6.
Figure 8:
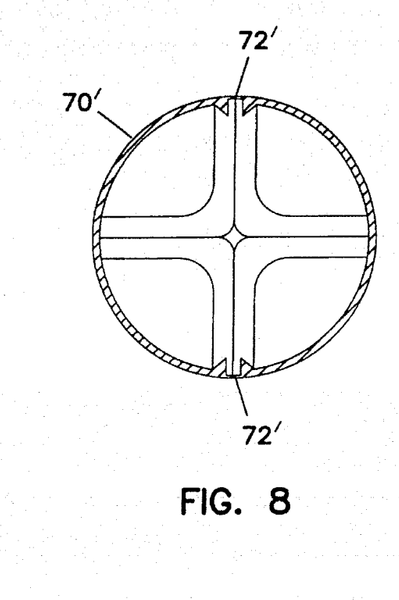
FIG. 8 is a view taken along line 8—8 in FIG. 6.

FIGS. 6–8 show an alternative embodiment of a protective sleeve 60' having a flanged end 64' and a distal end 62'. Attached to the flanged end 64' are ring-shaped handles 68' to be grasped by a user. The sleeve has a shaft portion 70' which is formed of polyethylene and includes reduced thickness portions 72' (about 0.005 inches thick) to permit the sleeve 70' to be split in half and removed following insertion of the plug.

From the foregoing description, it will be appreciated that the present device presents an incontinence plug which anchors at the bladder neck and seals against the urethral wall at a point positioned between the urethral sphincter and the bladder. The device may be formed of molded plastic which is lubricious or provided with a lubricious coating to prevent trauma to the urethra on insertion. The novel anchor 20'–22' is manipulated to have two positions, one for ease of insertion and the other to retain the device within the bladder. Additionally, the use of the protective sleeve helps avoid pathogen transmission from the meatus of the urethra into the interior of the urethra or the bladder.

From the foregoing detailed description of the present invention, it has been shown how the objects of the invention have been achieved in a preferred manner. Modifications and equivalents of the disclosed concepts such as those which readily occur to one skilled in the art are intended to be included in the scope of the appended claims.

What is claimed is:

1. A device for abating involuntary urine flow through an urethra extending from a pathogen-laden meatus to a bladder neck, said device comprising:

a plug sized to be inserted at least partially into said urethra by initial insertion of a distal end of said plug past said meatus and advancing said distal end toward said bladder neck to an inserted position with said plug in said inserted position abating said urine flow;

a protective sleeve coupled to said plug and surrounding said distal end with said sleeve presenting a barrier to pathogen transfer from said meatus to said distal end upon said insertion of said distal end past said meatus said sleeve sized to extend into said urethra a distance less than a distance of said distal end at said inserted position;

said sleeve movable coupled to said plug for said sleeve to be moved to a fully inserted position while maintaining said sleeve surrounding said distal end and presenting said barrier to pathogen transfer and with said distal end advanced past said sleeve upon further insertion of said plug a distance into said urethra beyond said distance of insertion of said sleeve at said fully inserted position whereby said sleeve prevents pathogen transfer to said distal end and said sleeve is only partially inserted into said urethra a distance less than a distance of insertion of said plug to minimize a distance a pathogen transportation by said sleeve.

2. A device according to claim 1 wherein said sleeve includes means for stopping advancement of said sleeve into said urethra after said plug has been partially inserted into said urethra but before said plug has been fully inserted into said urethra.

3. A plug for abating incontinence, said plug comprising:

a flexible body having a distal end and a proximal end with a length therebetween for said distal end to extend beyond a bladder opening when said proximal end is positioned against a meatus of a patient; and an anchor carried adjacent said distal end and protruding into said bladder to resist unintentional removal of said plug from said urethra, said anchor having a generally hollow, hemispherical geometry with external surfaces of said anchor sized to be act against said bladder at said bladder neck and surrounding said urethra, said anchor flexible to collapse to a reduced diameter state for insertion and removal.

4. A plug according to claim 3 comprising flow blocking means disposed on said body and disposed between said distal end and said proximal end with said flow blocking means sized to sealingly abut a wall of said urethra between said bladder and said meatus.

5. A plug according to claim 4 wherein said flow blocking means comprises an enlargement of said body.

6. A plug according to claim 5 wherein said flow blocking means is hollow and pliable in response to forces acting on said flow blocking means.

7. A plug according to claim 4 wherein said flow blocking means is positioned on said body to be disposed between a sphincter of said urethra and said bladder upon full insertion of said plug into said urethra.

8. A plug according to claim 3 wherein said anchor is opened to have an open end of said hemisphere facing outwardly away from said proximal end when in a rest position.

9. A plug according to claim 3 wherein said anchor is opened to have an open end of said hemisphere facing toward said proximal end when in a rest position.

10. A method for abating involuntary urine flow through an urethra extending from a pathogen-laden meatus to a bladder neck, said method comprising:

selecting a plug sized to be inserted at least partially into said urethra by initial insertion of a distal end of said plug past said a meatus and advancing said distal end toward said bladder neck to an inserted position with said plug in said inserted position abating said urine flow and with said plug having a protective sleeve coupled to said plug and surrounding said distal end with said sleeve presenting a barrier to pathogen transfer from said meatus to said distal end upon said insertion of said distal end past said meatus and with said sleeve sized to extend into said urethra a distance less than a distance of said distal end at said inserted position and with said sleeve movable coupled to said plug for said sleeve to be moved to a fully inserted position while maintaining said sleeve surrounding said distal end and presenting said barrier to pathogen transfer and with said distal end advanced past said sleeve upon further insertion of said plug a distance into said urethra beyond said distance of insertion of said sleeve at said fully inserted position;

inserting said plug and said sleeve into said urethra through said meatus with said sleeve surrounding said distal end;

advancing said distal end toward said bladder neck with sad distal end advancing past said sleeve to a fully inserted plug position distanced from said meatus greater than a distance of a leading end of said sleeve from said meatus whereby said sleeve prevents pathogen transfer to said distal end and said sleeve is only partially inserted into said urethra a distance less than a distance of insertion of said plug to minimize a distance a pathogen transportation by said sleeve.

* * * * *

UNITED STATES PATENT AND TRADEMARK OFFICE
CERTIFICATE OF CORRECTION

PATENT NO. : 5,513,659

DATED : May 7, 1996

INVENTOR(S) : Buuck et al.

It is certified that error appears in the above-identified patent and that said Letters Patent is hereby corrected as shown below:

Col. 5, line 48 delete "be" after the word "to"

Col. 6, line 46 "sad" should read --said--

Signed and Sealed this

Seventeenth Day of December, 1996

Attest:

BRUCE LEHMAN

Attesting Officer     Commissioner of Patents and Trademarks